United States Patent [19]
Sodis et al.

[11] Patent Number: 5,637,290
[45] Date of Patent: Jun. 10, 1997

[54] ORAL HYGIENE PRODUCT INCLUDING CHIOS MASTIC OIL

[75] Inventors: Michalis Sodis; George Sodis, both of Athens, Greece

[73] Assignee: Leather Line Imports, Inc., Frisco, Tex.

[21] Appl. No.: 549,128

[22] Filed: Oct. 27, 1995

[30] Foreign Application Priority Data

Jun. 28, 1995 [GR] Greece ............................ 950100243

[51] Int. Cl.$^6$ ............................................. A61K 7/16
[52] U.S. Cl. .................................................. 424/49
[58] Field of Search ..................................... 424/49

[56] References Cited

PUBLICATIONS

Boelens, M. et al., Flavour Fragrance J (1991) 6(4) 271–5.
Scrubis, B. et al. Int. Flavours Food Addit. (1975) 6(6) 349–356.
Melanitou, M. et al., Dev. Food Sci (1995) 37B 1937–45.
Papanicolaou, D et al, Dev. Food Sci (1995) 37A 303–10.

Primary Examiner—Paul J. Killos
Attorney, Agent, or Firm—John E. Vandigriff

[57] ABSTRACT

The invention is to the use of natural mastic from chios or extract mastic oil, or synthetic mastic agents for the production of toothpaste, mouth wash, mouth deodorizers, suntan lotions, hair products and cosmetics. Chios mastic and the extracted mastic oil have chemical reactions with the polymorph-nucleus causing the gathering of the white blood corpuscles resulting in the increase of the tissue defense system situated between the teeth and their gums acting against plague and the formation of gum disease.

6 Claims, 1 Drawing Sheet

ORAL HYGIENE PRODUCT INCLUDING CHIOS MASTIC OIL

FIELD OF THE INVENTION

The invention relates to products for personal use and more particularly to the use of mastic oil and synthetic mastic oil agents as basic ingredients for toothpastes, mouth wash, suntan lotions, hair products and cosmetics.

BACKGROUND OF THE INVENTION

In general, toothpastes contain several ingredients: an insoluble polishing agent, a binder, flavoring, and a liquid to give plasticity. The polishing agents most commonly used are phosphate salts such as dicalcium phosphate, calcium pyrophosphate, and insoluble sodium metaphosphate. Gum tragacanth and seaweed derivatives or cellulose derivatives are employed as binders. A wide variety of flavoring oils is used to give products a distinctive and pleasant taste; in post pastes, saccharin or cyclamate is added for sweetening, and often both are used. For liquid, almost all toothpastes employ glycerin and water. Tooth powders are essentially identical with toothpaste except that they contain no liquid and that the binder is sometimes omitted.

The search for agents that could be combined with a dentifrice safely and effectively to prevents caries (tooth decay) led to long experimentation with various compounds, culminating in 1960 with the discovery that stannous fluoride was effective against tooth decay. In the 1980s dentifrice were introduced that contained (1) agents that improve the effectiveness of brushing by loosening plaque, and (2) antimicrobial chemicals that help to prevent plaque buildup.

Sir Alexander Fleming, who discovered penicillin, found a substance called lysozyme in many secretions of the body, and in certain other plant and animal substances. Lysozyme has strong antimicrobial activity.

The use of antimicrobial chemicals and/or substances that attract and/or enhance lysozyme secretions are desirable to prevent plaque build-up on the teeth.

Mastic resin, obtained from the mastic tree, Pistacia lentiscus, has been used as an astringent, and has been used as an ingredient of varnishes and lacquers. It is also used as an ingredient of cement called asphalt mastic.

SUMMARY OF THE INVENTION

Personal health and hygiene products such as toothpaste, mouth wash, mouth deodorizers, and suntan lotion are made utilizing natural mastic from Chios, or extract mastic agents. Oral hygiene products including tooth paste are made utilizing at least several ingredients selected from oil, methyl paraden, methyl cellulose, menthol, alcohol, saccharine, tween, glycerine, sodium carbonate, aerosil, texapon K12, allantoine, camomile, and natural mastic oil, or an extract of mastic gum.

The technical advance represented by the invention, as well as the objects thereof, will become apparent from the following description of a preferred embodiment of the invention when considered in conjunction with the accompanying drawings, and the novel features set forth in the appended claims.

BRIEF DESCRIPTION OF THE DRAWINGS

The sole FIGURE of the application illustrates a basic process for producing the products utilizing mastic oil.

DESCRIPTION OF A PREFERRED EMBODIMENT

Figure 1:
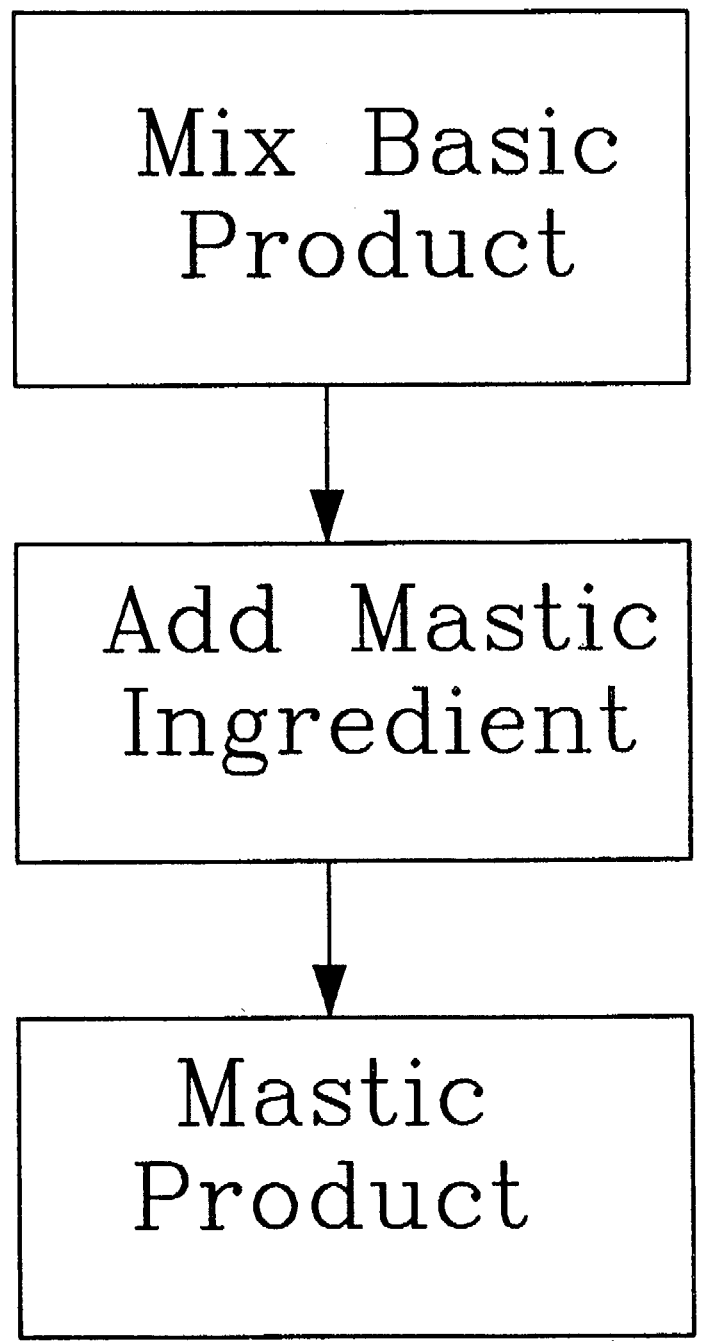

The sole FIGURE of the application shows a process whereby a mixture of ingredients 10 for personal hygiene products, such as tooth paste and mouth washes, can be mixed with one of mastic resin and extracts of mastic resin 11 to produce a tooth paste or mouthwash 12 including the products of the tooth paste material, or mouth wash, and mastic resin.

The introduction of mastic resin or extracts thereof provide beneficial results in the removal and prevention of plaque build-up on teeth.

White blood corpuscles, especially the polymorph-nucleus as blood components found in the liquid of the fissure, situated where the teeth join the gums act as the first defense system of the area before the development of clinical gum disease. Harmful properties such as the microbes that gather around the necks of teeth near the gums cause plague. Natural extracts of mastic chemically reacts with the polymorph-nucleus causing the gathering of white blood corpuscles, resulting in the increase of the defense system of the tissues in the area, and decrease the formation of plaque and gum disease. The introduction of mastic oil and/or extracts of mastic gum into toothpaste, mouthwash helps to reduce plaque and gum diseases while simultaneously serving as an antiseptic and mouth deodorant.

Oral hygiene products such as tooth paste are made utilizing several ingredients selected from oil, methyl paraden, methyl cellulose, menthol, alcohol, saccharine, tween, glycerine, sodium carbonate, aerosil, texapon K12, allantoine, camomile, and natural mastic oil, or an extract of mastic gum. The basic tooth paste product is made using some or all of these elements, and then the natural mastic oil, or an extract of mastic gum is added to the mixture. As an example, a tooth paste may be made utilizing the above ingredients, in addition to or as a substitute for other ingredients, in the amounts indicated: Methyl Parben in an amount of 0.08 to 0.2 percent; Ethyl Cellulose in an amount of 0.5 to 1.5 percent; Menthol in an amount of 0.08 to 0.25 percent; Alcohol in an amount of 0.2 to 0.6 percent; Saccharine Sodium in an amount of 0.01 to 0.03 percent; Asportame in an amount of 0.02 to 0.04 percent; Mastic Oil or extract in an amount of 0.5 to 0.6 percent; Tween 60 in an amount of 0.4 to 0.6 percent; Glycerine in an amount of 10 to 30 percent; Carbonate in an amount of 15 to 45 percent; aerosil 300 in an amount of 1.0 to 4.0 percent; Texapan K12 in an amount of 0.8 to 2.4 percent; and deionized water in an amount of about 12 to 16 percent.

The combination of mastic oil and other chemical substances such as a basic sunburn lotion can prevent sun burn. The mastic oil is added to a basic sunburn lotion, or a commercially available sunburn lotion to enhance its properties of sunburn prevention.

Mastic gum, oil and abstracts thereof may also be used in combination with cosmetics products for the face and body, and in the production of hair shampoo, hair emollient and body shampoos.

What is claim:

1. An oral hygiene product comprising the combination of a tooth paste and an ingredient selected from natural mastic from Chios, extracted mastic oil, and synthetic mastic oil agents.

2. The product according to claim 1, wherein said tooth paste includes ingredients selected from oil, methyl paraden, methyl cellulose, menthol, alcohol, saccharine, tween, glycerine, sodium carbonate, aerosil, texapon K12, allantoine, camomile, and deionize water.

3. The product according to claim 1, wherein the ingredient selected from natural mastic from Chios, extracted mastic oil, and synthetic mastic oil agents is combined with mouth wash.

4. The product according to claim 1, wherein the ingredient selected from natural mastic from Chios, extracted mastic oil, and synthetic mastic oil agents is combined with a cosmetic product.

5. An anti-plaque tooth paste, comprising:

a tooth paste base; and an ingredient selected from natural mastic from Chios, extracted mastic oil, and synthetic mastic oil agents.

6. The anti-plaque tooth paste according to claim 5, wherein said tooth paste base is composed of ingredients selected from oil, methyl paraden, methyl cellulose, menthol, alcohol, saccharine, tween, glycerine, sodium carbonate, aerosil, texapon K12, allantoine, and camomile.

* * * * *